US009562879B2

(12) United States Patent
Hirmer et al.

(10) Patent No.: US 9,562,879 B2
(45) Date of Patent: Feb. 7, 2017

(54) PIPE CONTAINING A METAL CASING WITH A PLASTICS MATERIAL INLAY FOR USE IN LOW AND HIGH PRESSURE APPLICATIONS, IN PARTICULAR AS AN HPLC COLUMN

(75) Inventors: Frank Hirmer, Schlitz (DE); Michael Frank, Grossenluder (DE)

(73) Assignee: MOLLER MEDICAL GMBH (DE)

( * ) Notice: Subject to any disclaimer, the term of this patent is extended or adjusted under 35 U.S.C. 154(b) by 318 days.

(21) Appl. No.: 14/239,256

(22) PCT Filed: Aug. 9, 2012

(86) PCT No.: PCT/IB2012/001629
§ 371 (c)(1),
(2), (4) Date: Feb. 17, 2014

(87) PCT Pub. No.: WO2013/024345
PCT Pub. Date: Feb. 21, 2013

(65) Prior Publication Data
US 2014/0196524 A1     Jul. 17, 2014

(30) Foreign Application Priority Data
Aug. 15, 2011 (CH) ...................... 1337/11

(51) Int. Cl.
*G01N 30/60* (2006.01)
*F16L 9/147* (2006.01)
(Continued)

(52) U.S. Cl.
CPC ............... *G01N 30/60* (2013.01); *F16L 9/147* (2013.01); *F16L 15/008* (2013.01); *F16L 19/00* (2013.01);
(Continued)

(58) Field of Classification Search
CPC  G01N 30/60; G01N 30/6004; G01N 30/6026; G01N 30/6039; G01N 30/6052; F16L 15/008; F16L 19/00; F16L 9/147
See application file for complete search history.

(56) References Cited

U.S. PATENT DOCUMENTS 5,074,599 A * 12/1991 Wirbel .................... F16L 47/04
                                                         285/341
5,736,036 A    4/1998 Upchurch
(Continued)

FOREIGN PATENT DOCUMENTS

DE     102008059897 A1    6/2010
DE     102009022368 B3    11/2010
(Continued)

*Primary Examiner* — Hezron E Williams
*Assistant Examiner* — David Z Huang
(74) *Attorney, Agent, or Firm* — Morriss O'Bryant Compagni, PC

(57) ABSTRACT

A chromatography column comprises a pipe that contains a tubular metal casing with an inlay and sealing ring. The inlay is configured as a plastics material tube and is pushed or drawn into the metal casing and a sealing ring of plastics material is connected to the inlay at the end. Because of this structure, a connection to further system parts is possible, which is carry-over-free, inert on the inside, liquid-tight, optionally gas-tight, and pressure-tight. A connection element and connection connect the pipe to feed and/or discharge lines of a capillary system. Pipes, connection elements and connections of this type are advantageously used in low and high pressure systems, such as, for example, in an HPLC column. The use of such systems is advantageous in in-vitro diagnostics and in liquid handling applications.

35 Claims, 10 Drawing Sheets

Figure 1:
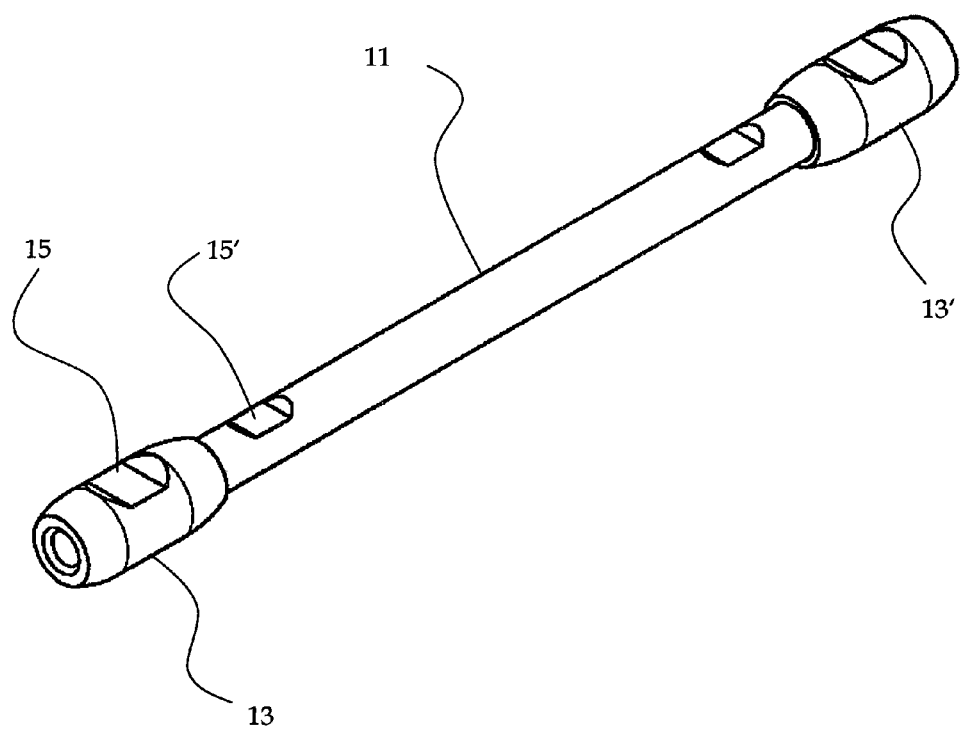

(51) Int. Cl.
*F16L 15/00* (2006.01)
*F16L 19/00* (2006.01)
(52) U.S. Cl.
CPC ...... *G01N 30/6004* (2013.01); *G01N 30/6026* (2013.01); *G01N 30/6039* (2013.01); *G01N 30/6052* (2013.01); *G01N 30/6073* (2013.01)

(56) References Cited

U.S. PATENT DOCUMENTS

| | | | |
|---|---|---|---|
| 6,352,266 B1 * | 3/2002 | Rigoli | G01N 30/6026 210/198.2 |
| 6,494,500 B1 * | 12/2002 | Todosiev | G01N 30/6026 285/279 |
| 2005/0199540 A1 | 9/2005 | Zelechonok | |

FOREIGN PATENT DOCUMENTS

| | | |
|---|---|---|
| EP | 2315022 A1 | 4/2011 |
| GB | 2238257 A | 5/1991 |
| JP | 9184831 A | 7/1997 |
| WO | 2011076244 A1 | 6/2011 |

* cited by examiner

PIPE CONTAINING A METAL CASING WITH A PLASTICS MATERIAL INLAY FOR USE IN LOW AND HIGH PRESSURE APPLICATIONS, IN PARTICULAR AS AN HPLC COLUMN

CROSS-REFERENCE TO RELATED APPLICATIONS

This application is a national phase entry under 35 U.S.C. §371 of PCT/IB2012/001629 filed Aug. 9, 2012, which claims priority to Swiss Patent Application No. 1337/2011 filed Aug. 15, 2011, the entirety of each of which is incorporated by this reference.

BACKGROUND OF THE INVENTION

Technical Area of the Invention

The invention relates to a pipe, in particular configured as a chromatography column, for example a high performance liquid chromatography column, which has a metal casing with an inlay. Furthermore, the invention relates to a connection element for connecting a pipe of this type to a feed or discharge line. The invention also relates to a connection system or low and high pressure system, in particular configured as a chromatography system, especially, for example, a high pressure liquid chromatography system, comprising at least one pipe of this type and optionally a connection element of this type. The invention furthermore relates to a connection for a capillary system, in particular an HPLC system, containing a plastics material pressed body with a through-opening.

Prior Art

High performance liquid chromatography (HPLC) is an established method for the chemical analysis and separation of substance mixtures. The method belongs to the standard equipment of a laboratory in research and industry. In particular, this method tends to be used for in-vitro diagnostics. The basic principle is based on the different adherence energy of substances to be separated on a known substrate. For analysis, a substance mixture is brought into solution in a so-called mobile phase and the solution is then pressed at high pressure through a column of porous particles (stationary phase). Depending on the adsorption behaviour of the various substances on the stationary phase, the constituents of the substance mixture leave the separation column one after the other.

There is a need in the area of HPLC and, quite particularly, for HPLC applications in the area of in-vitro diagnostics, for bio-inert HPLC hardware. At no point of the HPLC apparatus is an ion exchange to take place between a metal part and the sample to be analysed by chromatography. Substance adherences, such as, for example, of proteins, or carry-overs are also to be avoided. Pipe systems which are, in particular, inert and low in carry-overs would therefore be desirable.

It has attempted, on the one hand, to solve these problems in that, for example, high-grade steel pipes were inertly coated on the inside or were provided with glass inlays. On the other hand, in the HPLC area, complete systems are generally used nowadays, containing columns, screw connections, frits and capillaries, which are manufactured completely from plastics material, in particular polyetheretherketone (PEEK).

The following drawbacks are produced from using pure plastics material column systems:

Only low pressures can be applied to the system for packing the column or for transportation of the sample through the column, as well as low operating pressures. Thus relatively long passage times of the sample result.

Frequently desired micro columns are not possible, or only possible to a limited extent, because of the higher pressures required.

Only pure PEEK columns are generally commercially available. Although frequently required so-called PEEKsil columns (composite of glass pipe encased by PEEK) are available, their connection generally has to firstly be adapted, which often causes problems for the user.

The threads are often relatively weak because of the material properties of the PEEK and can only withstand a correspondingly low torque.

The commercially available PEEK columns are expensive, as they are produced by a complex centrifugal method.

The column dimensions have to have a specific size (standard). Deviations mean high tool costs.

The following drawbacks are produced by using coated systems (coated high-grade steel):

The production of a gap-free coating is difficult; in particular it is not practicable to prove a gap-free coating over the complete internal diameter of the system. Consequently there is no process reliability.

With a different layer thickness, metal ions can diffuse into the sample at the points at which the coating is too thin.

The sealing at the end face or the transition between the coated pipe and connection fitting is not ideally solved.

The following drawbacks are produced from the use of glass inlay columns:

Glass inlay can easily break or rupture and can therefore become untight.

There is generally a gap between the glass inlay and high-grade steel and this leads to a break at elevated pressure. High pressures can therefore not be applied.

The sealing at the end face or the transition between the HPLC column with the glass inlay and connection fitting is not yet ideally solved.

The published application WO 2011/076244 A1 relates to an assembly element for a fluidics device, in particular for applications in devices for high performance liquid chromatography. An assembly element of a fluid coupling for coupling a pipeline to a fluidics device is disclosed. The assembly element contains a pipeline with an inlay, the inlay being located in a cavity of a front side of the pipeline and projecting slightly out of the line. The inlay is used for sealing during coupling to a chromatography device. The pipeline, depending on the application, may have a plastics material (for example PEEK) on the inside. The drawback here is, in particular, that the connection takes place upon coupling over said inlay so that not only one joint is produced but simultaneously two joints between the pipeline and its coupling partner. Each additional connection point harbours the danger of contamination and carry-over of impurities. In addition—depending on the embodiment of the pipe—the effective connection face of the insert and innermost pipeline layer is optionally very small, which additionally reduces the reliability of the coupling system.

The published application EP 2 315 022 A1 shows a chromatography column with a frit ring, frit holder and end connection. The sealing of this system extends over a plurality of joint connections between the pipe and frit ring, frit ring and frit holder as well as frit holder and end connection. With this structure, the numerous connection points (joint points) being produced during the coupling, are problematical with regard to a carry-over of impurities and contamination.

A biocompatible liquid chromatography column is described in the U.S. Pat. No. 5,736,036. The inner pipe of the column is integral and can therefore not be pulled through the outer pipe or separated. An axial slipping of the inner pipe relative to the outer pipe is thus ruled out. In terms of manufacturing, restrictions are imposed by this structure. In particular, the inner pipe is introduced by a casting method. During casting, a material-uniting connection is formed between the outer and inner pipe. The drawback in the casting method are the increased manufacturing costs, which in particular also arise in that with the desired thickness variation of the inner pipe, the latter cannot easily be exchanged, but the column in each case has to be manufactured in various configurations. The outlay to produce various combinations of inlay thicknesses and column lengths and to have them in stock correspondingly has to be rated as high. In addition, because of the cast manufacturing, bubbles may form, which reduce the effective wall thickness of the inner pipe. In addition, checking for bubbles is difficult in the completed pipe composite.

Advantages of the Invention

An advantage of the present invention is to provide in-vitro diagnostic systems or liquid handling systems or parts for use in systems of this type. Furthermore, it is an advantage of the present invention to provide an inert or bio-inert high performance liquid chromatography system (HPLC system), which does not have the drawbacks of the prior art or at least partially avoids them. In particular, one aim is to provide an inert HPLC column, which combines the advantages of the known plastics material columns and metal columns.

DESCRIPTION OF THE INVENTION

The foregoing advantages are achieved by a pipe, that may be configured as a chromatography column, containing a tubular metal casing with an inlay and sealing ring, which pipe is characterised in that the inlay is configured as a plastics material tube (or plastics material pipe) and is pushed or drawn into the metal casing and a sealing ring (in particular a sealing ring in each case), consisting of plastics material is connected to the inlay at the end face or at the end of the pipe. Because of said structure of the pipe, a liquid-tight or gas-tight connection to other system parts is optionally possible. The inlay can also be called a covering. The metal casing is thus covered on the inside with the covering (or the inlay). The advantages of this pipe are, in particular, its simple and economical manufacture. The pipe and inlay are, in particular, not connected in a material uniting manner, but adjoin one another, optionally with a fit, in particular press fit.

Further advantages and features of the invention emerge from the following description.

The pipe is expediently used as a high performance liquid chromatography column (HPLC column). At each end of the pipe, a sealing ring mentioned is, in each case, expediently connected to the inlay.

The inlay advantageously pushes through the sealing ring or the sealing rings or—expressed differently—the inlay is drawn through the sealing ring or the sealing rings. The sealing ring may adjoin the lateral surface of the inlay on the outside, or rest thereon. The inlay and sealing ring may be connected to one another in a material-uniting manner. The advantages of this arrangement are that the inlay tube remains free at its end face in order to undergo a direct sealing connection with the part to be connected, only one joint point being produced per connection between the inlay and connection part. The sealing ring encompassing the inlay tube on the casing side on the one hand has a supporting effect on the inlay end region and, on the other hand, it widens the sealing face at the joint point to the connection part. In addition, the face between the sealing ring and inlay can be adapted or optimised by the choice of sealing ring length.

The pipe according to the invention may be part of an in-vitro diagnostic system or a liquid handling system. Chemical analysis systems and preparative instruments are examples of liquid handling systems of this type and optionally in-vitro diagnostic systems.

An annular depression is advantageously recessed on the end face or on the end face of the metal casing on the inside of the casing, which depressions receive the sealing ring. Optionally, an annular depression is in each case recessed at the two end faces or on the end face of the metal casing on the inside of the casing.

Alternatively, the inlay projects on the end face, in particular at the two end faces of the metal casing, so that the sealing ring or the sealing rings adjoin the inlay on the outside (in particular so the sealing ring adjoins the lateral surface of the inlay on the outside), or encompass the inlay adjacently and are optionally integrally connected thereto in a material-uniting manner.

Advantageously, edge regions of the metal casing located radially outwardly on the end face are not occupied or covered by the sealing rings.

The sealing ring may be applied to the metal casing and/or the inlay by injection-molding. The inlay and sealing material may be welded, in particular laser-welded or glued, in order to produce an integral (i.e. one-piece or material-uniting) material bond.

The material of the inlay and/or the sealing ring may contain a thermoplastics material, in particular selected from the group consisting of fluoroplastics (also called fluoropolymers), polyaryletherketones (PAEK) and mixtures thereof, the polyaryletherketones may be selected from the group consisting of polyetherketone (PEK), polyetheretherketone (PEEK) and polyetherketoneketone (PEKK), polyetheretherketone (PEEK) being more desireable, and polytetrafluoroethylene (PTFE) being preferred desired fluoroplastics material. The plastics material of the inlay and the sealing ring may consist of the same material group, or in particular of the same material, such as PEEK.

In an alternative embodiment, the plastics material inlay may encase a glass capillary. The plastics material of an inlay of this type may also be selected from the group consisting of fluoroplastics and polyaryletherketones (PAEK). For example, a PEEK capillary may be used with an inner glass capillary. Polytetrafluoroethylene (PTFE) or a composite or a mixed material containing at least one PAEK plastics material and PTFE is also suitable, in particular for encasing the glass capillary.

The wall thickness of the inlay is advantageously in the range from 0.05 mm to 2 mm, in particular in the range from 0.1 mm to 1 mm.

The metal casing being used to support the inner plastics material parts may substantially consists of high-grade steel. In addition, the internal diameter of the metal casing may be in the range from 0.5 mm to 10 mm, or in the range from 2 mm to 6 mm.

According to the present invention, there is no material-uniting connection between the metal casing and inlay. However, the possibility exists of producing a press fit between the inlay and metal casing with a corresponding selection of the outer inlay diameter and inner metal casing diameter for better slip-resistance, in that the inner metal casing diameter is selected to be slightly smaller than the outer inlay diameter.

The internal diameter of the sealing ring expediently substantially corresponds to the external diameter of the inlay at the edge regions thereof. The inlay in the edge region is advantageously welded or glued to the inner wall of the sealing ring.

A thread is expediently formed in at the pipe end region, in particular at each of the two pipe end regions. Other embodiments are conceivable, however.

The above advantage is furthermore advantageously achieved by a connection element for connecting a pipe according to the invention, in particular a chromatography column such as, for example, a high performance liquid chromatography column, to a feed or discharge line, in particular a sample feed or sample discharge line. The connection element comprises a cylindrical metal casing. This metal casing comprises a first end, a centre piece and a second end, an internal thread being formed in at the first end, the second end being configured as a connection piece for the feed or discharge line and the centre piece containing a plastics material pressed body with a through-opening to receive one end of a feed or discharge line. The plastics material body can be inserted from the first end and abuts against a first internal shoulder of the metal casing. In the cavity of the first end, both the plastics material body and the tubular metal casing, which has a second internal shoulder, form a joint face for a pipe, in particular for a pipe of a chromatography column.

At the end face toward the first end, a filter may be let into the plastics material pressed body, optionally in a flush manner.

Furthermore, a connection system according to the invention (also called a low and high pressure system or low and high pressure line system here), in particular a chromatography system or high performance liquid chromatography system, is disclosed, which contains:

(a) a pipe according to the above statements, (b) a first connection element, in particular according to the above statements, for the sealing connection of a feed line, in particular a sample feed line, and (c) a second connection element, in particular according to the above statements, for the sealing connection of a discharge line, in particular a sample discharge line.

A connection system of this type or a low and high pressure system is inert relative to a sample material inasmuch as the plastics material used on the inside is inert under operating conditions (for example pressure and temperature) relative to the sample material. Systems which work at a pressure to a maximum of 1000 bar, or to a maximum of 500 bar, are called low pressure systems here. Systems, which are used at a pressure of 500 bar or more, in particular at a pressure from 1000 bar or more, are called high pressure systems here.

A connection system of this type or low and high pressure system is free of metal surfaces on the sample passage side. The sample and metallic casing parts can therefore not contact one another, so an ion exchange, material adhesions, such as, for example, protein adhesions or a carry-over are avoided.

Advantageously, a filter or a filter body is arranged in each case between the inlay and plastics material pressed body. The filter is may be selected from the group containing the filter fabric, screen and frits, in particular metal frits, sintered metal frits and PEEK frits. The material of such filters is expediently inert with respect to the sample material to be tested.

The plastics material pressed body and sealing ring may be dimensioned such that they contact one another in a sealing manner. The external diameter of the plastics material pressed body expediently substantially corresponds to the external diameter of the sealing ring, in particular the external diameter of the respective sealing ring.

Due to the construction, a first respective seal of plastics material on plastics material and a second respective seal of metal on metal advantageously exist between the pipe and each connection element.

The connection system or low and high pressure system may contain a feed and/or discharge line, the feed and/or discharge line may be configured as a plastics material tube (i.e. plastics material capillary) with a metal surround.

In the assembled state, a first seal of plastics material on plastics material and a second seal of metal on metal may exist between the connection element and feed or discharge line.

The respective first seal advantageously forms an inner seal and the respective second seal forms an outer seal. The inner seal here is optionally called a chemical seal and the outer seal is optionally called a hydraulic seal.

The so-called connection system is advantageously used in a low and high pressure line system, for example in a chromatography system or a high performance liquid chromatography system. The connection system is therefore suitable, in particular, for liquid handling systems and in-vitro diagnostic systems.

According to one exemplary embodiment, a pipe connection system for connecting two pipes is provided, in particular a pipe and a capillary (capillary configured here, for example, as a feed or discharge line), the pipe and the capillary each having a plastics material inlay, characterised by a cylindrical connection element, which, at its opposing ends, has a first and a second screw thread, and a receiving space in between for a pressed body, a pipe also having a screw thread, at the end face of which pipe a sealing ring is arranged, which is connected to the pipe inlay, a capillary with an inlay, which projects over the capillary end and defines a sealing portion, a screw part, which cooperates with one of the screw threads of the connection element and is used to fix the capillary on the connection element, and a pressed body for arrangement in the receiving space, which pressed body in the screwed state cooperates, on the one hand, with the sealing ring and, on the other hand, with the sealing portion, in a sealing manner.

The pressed body advantageously has a recess to receive the sealing portion. The sealing portion and pressed body are advantageously connected to one another in a material uniting manner.

The inlay is expediently formed by a plastics material tube, which is drawn into the pipe or into the capillary respectively.

The above-mentioned specification of the aim is furthermore achieved with a connection according to the invention of two capillaries of a capillary system, in particular of an HPLC system, which connection is constructed from at least one plastics material pressed body with a through-opening and is characterised in that a plastics material capillary (such as one plastics material capillary in each case on both sides of the through-opening) is connected to the through-opening, which plastics material capillary is encompassed at the end by a plastics material ring (i.e. a sealing ring), wherein at least the plastics material ring can be pressed or is pressed onto the plastics material pressed body. As a result, a tight, in particular liquid-tight, optionally gas-tight, seal of the connection is achieved.

The plastics material capillary and plastics material ring may form an integral bond, in particular a material-uniting bond. A material-uniting connection may, for example, be produced by welding, in particular by laser welding and/or injection-molding. Alternatively, the bond can be achieved by gluing.

The contact faces of the plastics material ring (i.e. the sealing ring) on the plastics material pressed body thus produce seals of plastics material on plastics material.

The plastics material pressed body and the plastics material capillaries are advantageously each encompassed by a metal casing. In this case, the metal casings may be connectable to one another, whereby a pressing power is produced in the connection.

The contact faces between the metal casing on the metal casing thus produce seals of metal on metal.

The plastics material used according to the invention is advantageously selected from the group of thermoplastics, in particular selected from fluoroplastics materials, polyaryletherketones (PAEK) and mixtures thereof, in particular selected from the group containing polytetrafluoroethylene (PTFE), polyetherketone (PEK), polyetheretherketone (PEEK), polyetherketoneketone (PEKK), polyetheretheretherketone (PEEEK), polyetherketoneetherketoneketone (PEKEKK), and polyetheretherketoneetherketone (PEEKEK), polyetherketone (PEK), polyetheretherketone (PEEK) and polyetherketoneketone (PEKK) being desired and polyetheretherketone (PEEK) being most desired.

According to the invention, the described pipe, the described connection element, the described connection system or low and high pressure system and/or the described connection for a capillary system can be used in an in-vitro diagnostic system or a liquid handling system. The pipe according to the invention (optionally in connection with the connection element according to the invention and/or using the connection according to the invention) is particularly suitable for use as a chromatography column or as a high performance liquid chromatography column (HPLC column).

An in-vitro diagnostic system or a liquid handling system, which is configured with a pipe according to the invention, optionally in connection with a connection element according to the invention, can be used, because of its inert properties over a broad application area.

SHORT DESCRIPTION OF THE FIGURES

Figure 2:
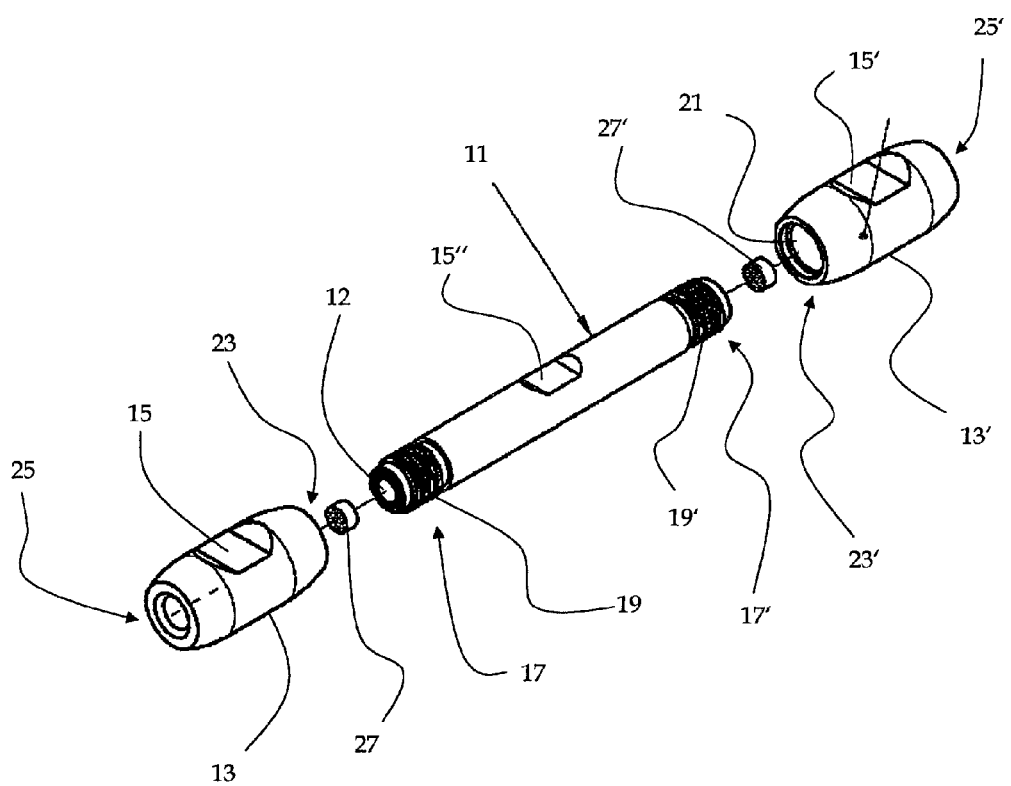
Figure 3:
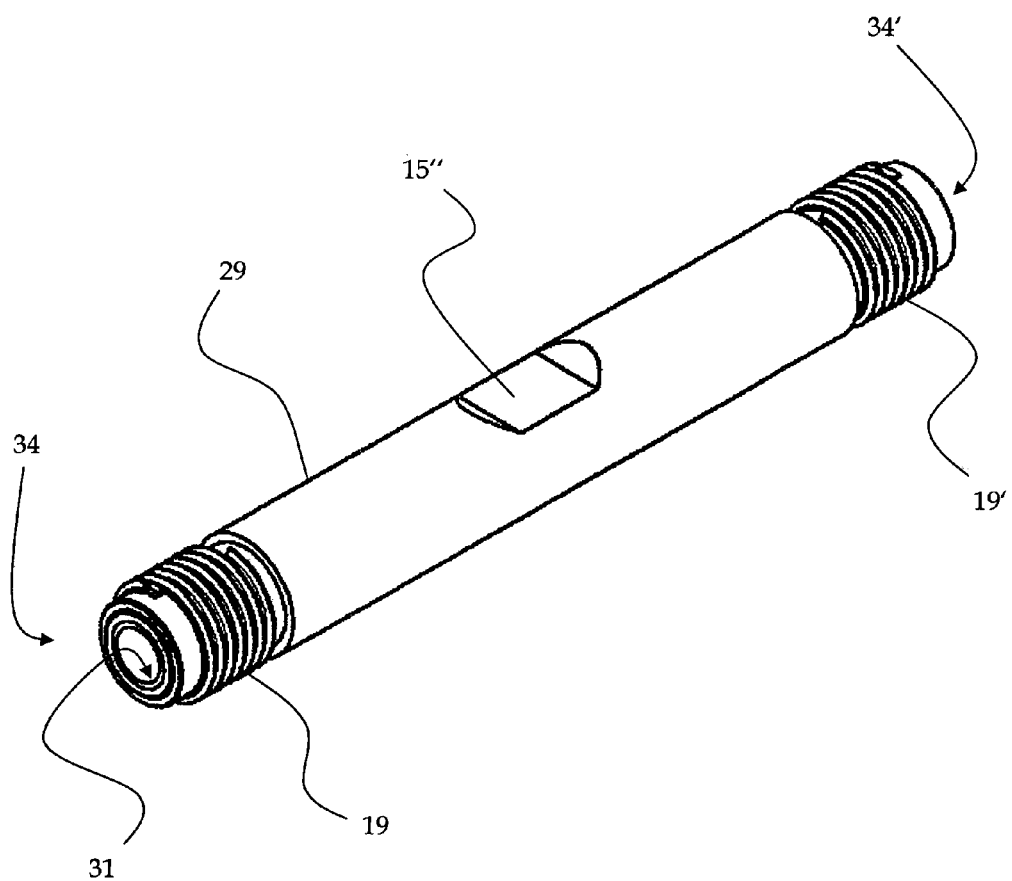
Figure 4:
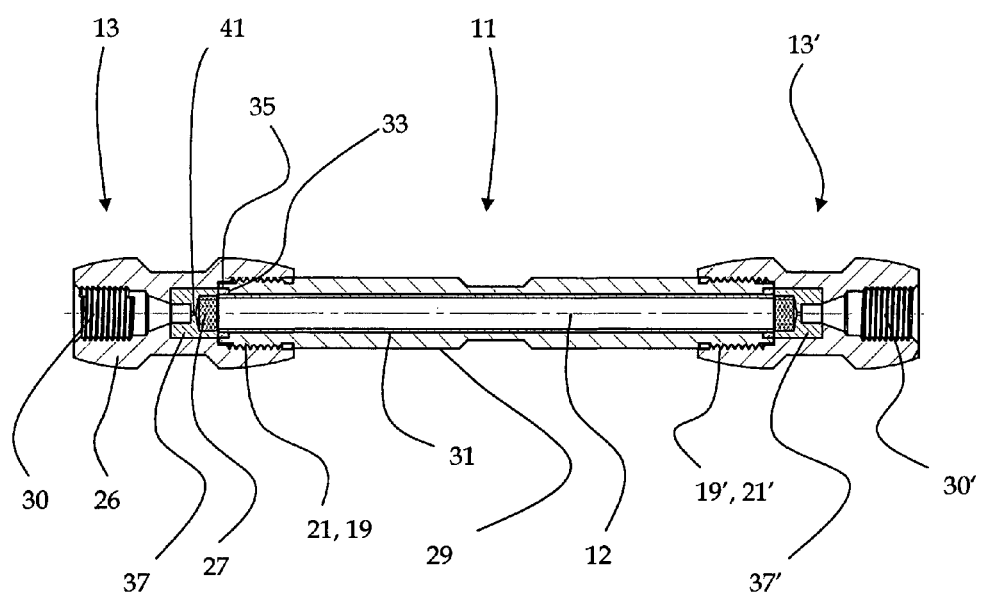
Figure 5:
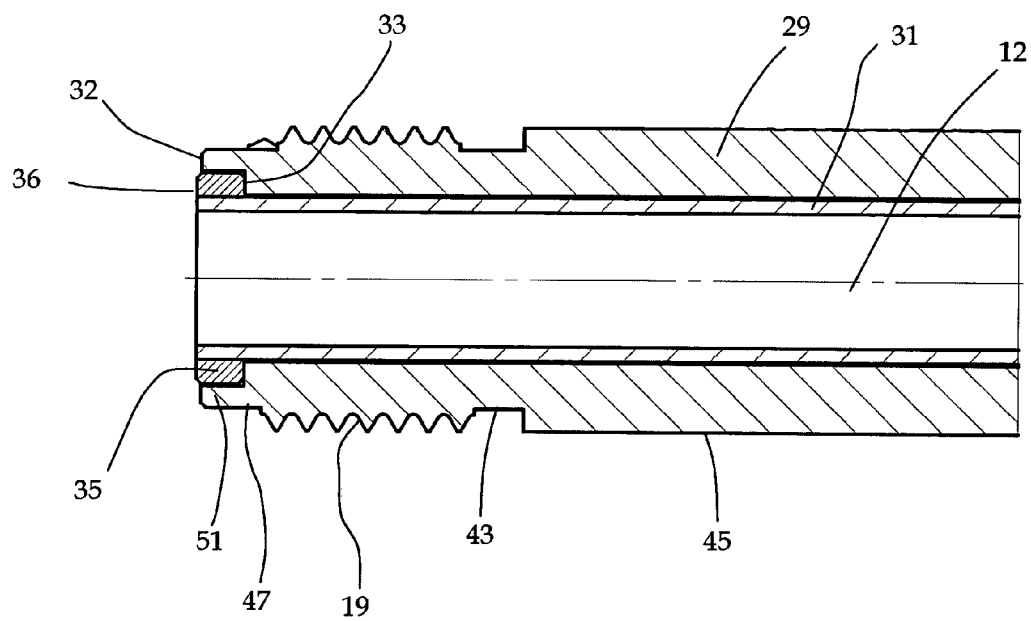
Figure 6:
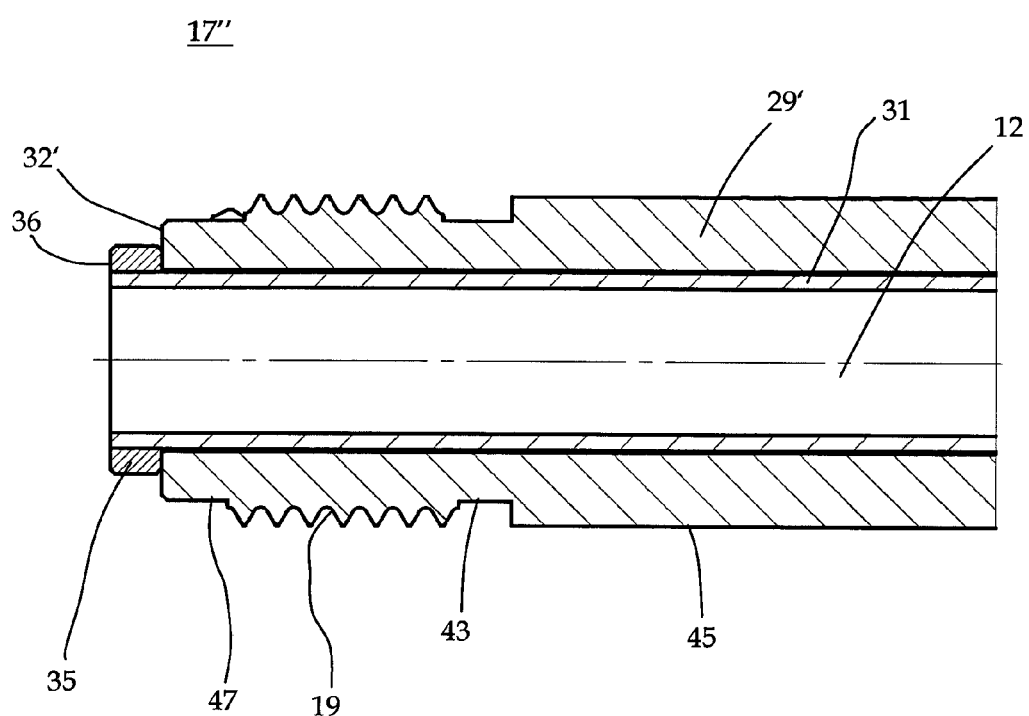
Figure 7:
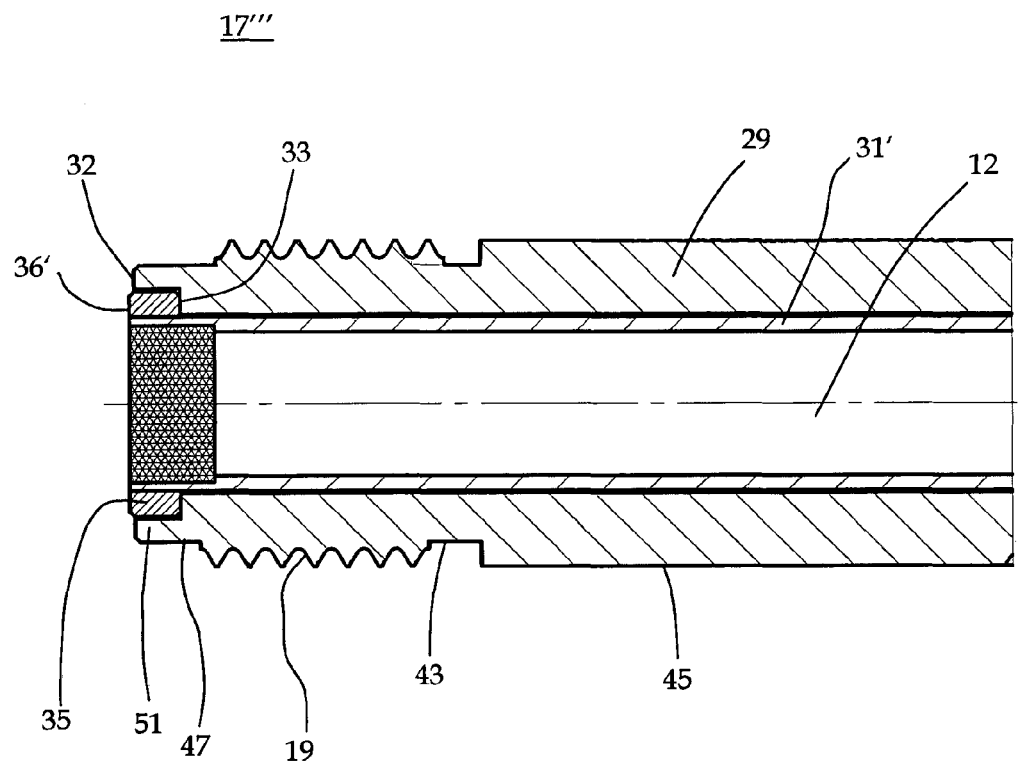
Figure 8:
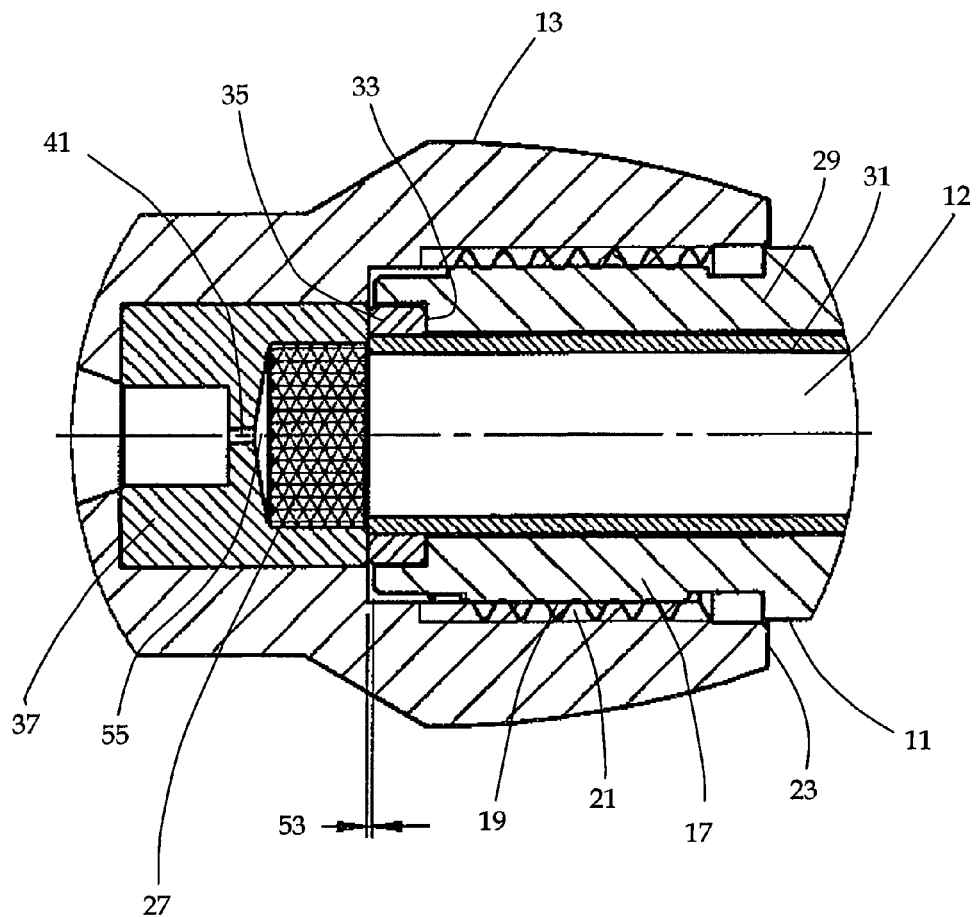
Figure 9:
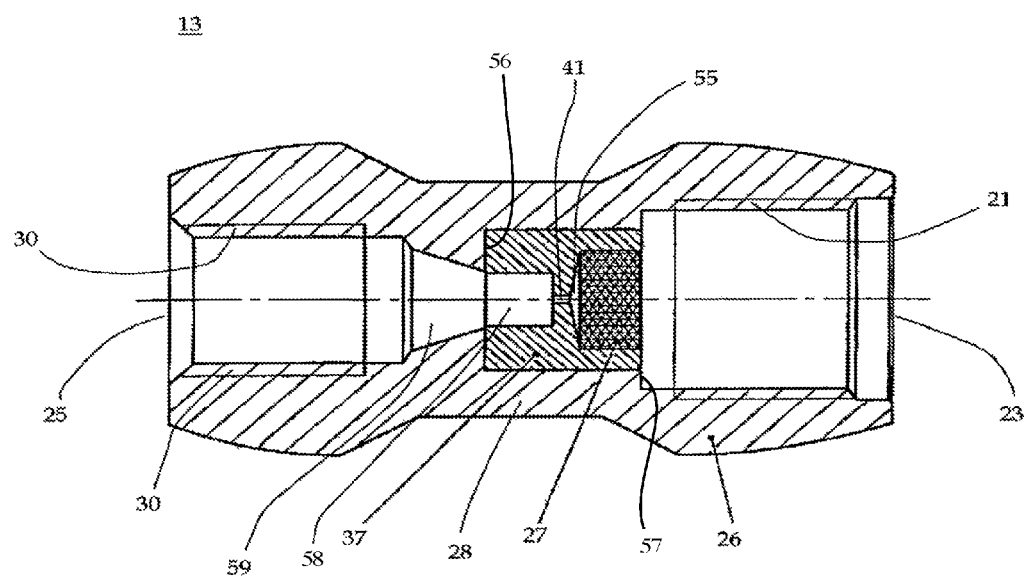
Figure 10:
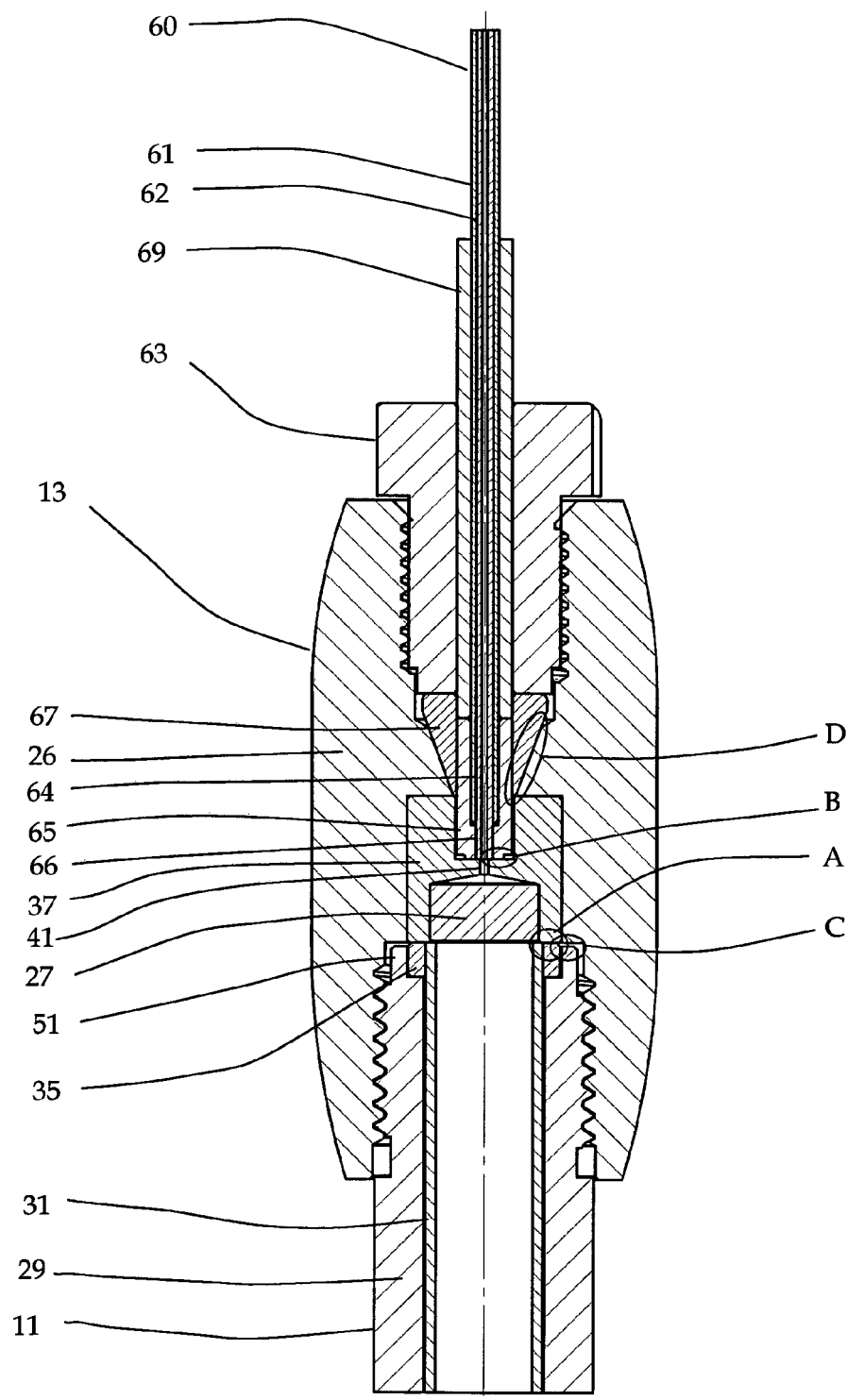

Other advantages and features of the invention emerge from the following description of exemplary embodiments with reference to figures. Features mentioned may be implemented in any combination—as long as they are not mutually exclusive. In the drawings, schematically:

FIG. 1: shows a perspective view of a system according to the invention with a chromatography column and connection parts;

FIG. 2: shows a perspective view of a disassembled system according to the invention with a chromatography column, two filters and two connection parts;

FIG. 3: shows a chromatography column according to the invention as in FIG. 2;

FIG. 4: shows a longitudinal section through a system with a chromatography column, two filters and two connection parts;

FIG. 5: shows a pipe end region according to the invention in longitudinal section of an embodiment as in FIG. 4;

FIG. 6: shows an alternative pipe end region according to the invention in longitudinal section;

FIG. 7: shows a further alternative pipe end region according to the invention in longitudinal section;

FIG. 8: shows a detail containing a pipe end region according to FIG. 5, which is screwed to a connection element, in longitudinal section;

FIG. 9: shows a longitudinal section of a connection element;

FIG. 10: shows a detail of a capillary device containing a connection element, which is connected at a first end to a pipe end and, at its second end, to a discharge or a feed line, in longitudinal section.

DESCRIPTION OF THE INVENTION WITH THE AID OF THE FIGURES

The same reference numerals stand for the same or functionally the same elements below. An additional apostrophe is used to distinguish a plurality of or alternative elements.

FIGS. 1 to 4 show a cylindrical pipe 11 with or without connection elements 13, 13'. The pipe 11 is, in particular, equipped as a chromatography column. A column of this type is used to receive a stationary phase (not shown) in the pipe interior 12, which a mobile phase (not shown) can flow through. The pipe interior 12 therefore forms a passage. If a substance mixture is fed to the mobile phase, the various constituents of the substance mixture separate, because of a different distribution of the constituents between the stationary and the mobile phase, into fractions transported at different speeds. The two ends of the pipe 11 are connected or can be connected, to connection elements 13, 13'. These connection elements 13, 13' are used to connect a feed or a discharge line (not shown) for sample material to the pipe, in particular to a chromatography column. For easier assembly, tool engagement points 15, 15', 15", which favour the holding and therefore the screwing of the pipe 11 and connection element 13, 13', are formed on the pipe 11 and on the connection elements 13, 13'. For example, each pipe end region 17, 17' has a thread (an external thread 19, 19', in particular, here), which can be screwed to a counter-thread (an internal thread 21, 21', in particular, here) of the connection element 13, 13'. Alternatively, other types of connection could be used, such as, for example, a plug mechanism with an anti-withdrawal device (for example a barbed hook).

Each connection element 13, 13' (here also called a fitting) according to FIGS. 1 to 4 has two connection points 23 and 25, or 23' and 25'; a first connection point 23, 23' is used for fastening on the pipe 11 and a second connection point 25, 25' is used for fastening on a feed or discharge line. A connection element 13, 13' is therefore used to connect the pipe 11 to a feed or discharge line. In the assembled state, it is possible to feed the pipe 11 with sample material at the end or to remove the material that has passed through the pipe passage and separated and to analyse it. A connection element 13, 13' contains at least one cylindrical base body 26 (FIG. 4), in particular manufactured from metal, a fitting insert 37 and selectively a filter 27. The base body 26 consists of at least the two connection points 23 and 25, or 23' and 25', which are connected to one another by a bridge part 28 located in between. The two connection points of a connection element are optionally arranged coaxially with respect to one another. Each connection point 23, 25 can be equipped with a thread, in particular an internal thread 21 or 30, or another fastening structure. The fitting insert 37 is also called a pressed body here. The fitting insert 37 is advantageously produced from a plastics material.

FIGS. 2 and 4 show filters 27, 27', which are arranged upstream and downstream of the pipe passage 12. A filter 27, 27' can be fitted in the pipe end region 17, 17', the connection element 13, 13' or partially in both. The filter 27, 27' may be exchangeable.

The pipe 11 consists, according to the invention at least of a metal casing 29 and an inlay 31. The ends of the pipe 11 have end faces 34, 34'. Faces which are visible in an axial plan view are called end faces here. The metal casing is manufactured from an inert metal or an inert metal alloy, such as from high-grade steel, and the inlay 31, is manufactured from a plastics material. The inlay 31 advantageously consists of a plastics material tube which, as shown in FIG. 3, for example, is drawn or pushed into the metal casing 29. The external diameter of the inlay 31 and the internal diameter of the metal casing 29 are substantially the same size, i.e. the inlay 31 may be seated in a taut manner in the metal casing 29. Alternatively, the external diameter of the inlay 31 can optionally be designed to be somewhat smaller than the internal diameter of the metal casing 29, in particular by a maximum of 100 micrometers, a maximum of 50 micrometers, or by a maximum of 5 micrometers. The inlay 31 and metal casing 29 are approximately the same length, the inlay 31 being dimensioned to ensure a tight pressure connection between the inlay 31 and connection elements 13, 13'. In one embodiment, the metal casing 29 has end threads 19, 19', in particular external threads, which are used for connection to discharge or feed lines, this connection expediently being able to take place by means of a connection element 13, 13' connected in between. The two threads 19, 19' may be placed on the outside in the pipe end regions 17, 17'.

In FIG. 4, a longitudinal section is shown through the pipe 11 and the screwed-on connection elements 13, 13'. The pipe 11 comprises a casing 2, in particular made of metal, which is covered over its entire inside with an inlay 31. As can be seen from the enlarged view in FIG. 5, a depression 33 on the inside of the casing can be formed at the end face of the metal casing 29, said depression being covered with a sealing ring 35. The sealing ring 35 therefore rests on the lateral surface of the inlay 31 at the end, at least on the outside. The contact faces between the inlay 31 and sealing ring 35 are advantageously welded or optionally glued and therefore form an integral, i.e. one-piece or material-uniting bond. If the sealing ring 35 is introduced into the depression 33 by injection-molding, an integral connection (i.e. a material-uniting connection) can optionally already be formed during the injection-molding production, which, depending on the application, makes additional welding superfluous. The pipe end region 17, 17' with a thread 19, 19' is received by the connection element 13, 13' with a non-positive connection. The end face 36 of the inlay 31 with a sealing ring 35 abuts in the connection element 13, 13', at least partially, on an insert 37. This insert 37 advantageously also consists of a plastics material. The contact faces between the insert 37 and sealing ring 35 form an annular face. When the pipe 11 and connection element 13, 13' are screwed, two plastics material faces therefore meet one another, and close under corresponding contact pressure, in a liquid-tight manner, optionally in a gas-tight manner. During screwing, the pipe casing 29 and the connection elements 13, 13' meet one another on the outside of the inlay. Advantageously, the end face 32 of the pipe casing meets a metal inner face of the connecting part 13, 13', so that with corresponding contact pressure and a corresponding orientation of the faces pressed against one another, this connection, which advantageously consists of two metal faces pressed against one another, is liquid-tight and optionally gas-tight. However, other constructions for the closure (optionally liquid-tight or gas-tight) between the metal pipe casing 29 and metal connection element 13, 13' would, however, also be conceivable.

By screwing or pressing the pipe 11 to or onto the connection element 13, 13', a liquid-tight (optionally gas-tight) through-passage is therefore produced, which leads from the interior of the inlay 31 through the filter 27 into a fine through-opening 41 in the fitting insert 37.

On the opposite side of the through-opening 41, the fitting insert 37 is configured in such a way that a feed or a discharge line can be inserted in a liquid-tight (optionally gas-tight) manner. Advantageously, a feed or discharge line also has a metal casing and an internal covering of plastics material. The second connection point 25, 25' of the connection element 13, 13' is configured in such a way that the two components of the feed or discharge line during connection to the connection element 13, 13' impinge on faces of the same material or similar material. In other words, the internal covering, which advantageously consists of plastics material, can be connected to the fitting insert 37 in a liquid-tight, optionally gas-tight manner (for example by contact pressure), and the casing, which is advantageously metallic, is connectable to metallic regions of the connection element 13, 13', in particular in a liquid-tight manner (optionally in a gas-tight manner).

The configuration of the pipe end regions 17 and alternative configurations of the pipe end regions 17" and 17'" will be described below with the aid of FIGS. 5, 6 and 7.

Embodiments of the pipe end region 17 (also correspondingly 17') of a pipe 11 are shown enlarged in FIGS. 5, 6 and 7—in particular in FIG. 5, that embodiment, which is also contained in FIG. 4, and alternative embodiments in FIGS. 6 and 7. The pipe substantially contains a metallic pipe casing 29, 29', which at the pipe end or at the end region, carries an external thread 19. The thread outlet 43 at the transition to the shaft may be configured as an indentation relative to the pipe casing external diameter of the shaft region 45. The thread outlet 47 at the end or near the end face can also have a reduced pipe casing external diameter in comparison to the shaft region 45. An inlay 31, 31' of plastics material is advantageously drawn as a tube into the metallic pipe casing 29, 29' or alternatively applied as a coating to the inside of the pipe casing 29, 29'. The inlay 31, 31' is reinforced at the end with a sealing ring 35, such as in a material-uniting manner. Advantageously, the two plastics materials of the inlay 31, 31' and sealing ring 35 are welded to one another and/or the sealing ring 35 was introduced by plastics material injection-molding; alternatively, an adhesive connection is conceivable, for example.

The sealing ring is matched in accordance with the application to the pipe casing 29, 29'. According to the advantageous embodiment shown, the sealing ring 35 is at least the same thickness as or thicker than, the wall thickness of the inlay 31, 31'. The external diameter of the sealing ring 35 is advantageously smaller than the external diameter of the pipe 11, advantageously smaller by at least 1 mm, or smaller by at least 1.5 mm.

In the embodiment of a pipe end region 17 according to FIG. 5, the sealing ring 35 rests at least partially in a depression 33 on the internal wall of the pipe casing 29. Advantageously, the depression is open at the end face, so the sealing ring 35 can optionally form an end face 36 with the inlay 31. A remaining edge region of the pipe casing 29 radially to the outside provides a type of support web 51. Optionally, the inlay 31 and/or the sealing ring 35 project slightly in axial extension, for example 0.1 mm to 2 mm, beyond the edge of the pipe casing 29, so these are compressed under pressing force and with the fitting insert 37 as the counter-piece, can form a gas-tight passage.

In the alternative embodiment of a pipe end region 17'' according to FIG. 6, the sealing ring 35 rests on the end face 32' of the pipe casing 29'. A support web 51, as shown in FIG. 5, is therefore dispensed with in this embodiment variant, but could be provided on the connection element. Because of the advantageous material-uniting connection between the inlay 31 and sealing ring 35, the inlay 31 is reinforced and supported at its end projecting over the pipe casing 29'.

In the embodiment of a pipe end region 17''' according to FIG. 7, the sealing ring 35 rests at least partially in a depression 33 on the internal wall of the pipe casing 29, as shown above in the embodiment according to FIG. 5. Advantageously, the depression is open on the end face and optionally a remaining edge region of the pipe casing 29 radially to the outside provides a type of support web 51. Optionally, the inlay 31' and/or the sealing ring 35 project slightly at the end in an axial extension beyond the edge of eh pipe casing 29. As shown in FIG. 7, the filter 27 may alternatively be let into the pipe 11 at the end face. In this case, the filter 27 is expediently surrounded by the inlay 31', so the tightness is ensured. Alternative embodiment variants are conceivable, in which the filter is partially let into the inlay 31' and therefore into the pipe 11 and partially into the fitting insert 37 of the connection element 13. However, it is important in all the variants that the structural configuration of the inlay 31, 31' with the fitting insert 37 allows a positive and gas-tight connection, for example by screwing or pressing the pipe 11 and connection element 13. At the same time, a positive and optionally gas-tight connection should also be adjusted between the metal faces of the pipe casing 29 and the connection element 13.

A configuration of a positive bond of the pipe 11 and connection element 13 will be shown below by FIG. 8. In this view, it is possible to see, above all, the state when the pipe 11 and connection element 13 are screwed. In particular, it can be seen that certain faces (i.e. end faces) of the sealing ring 35 and fitting insert 37 or inlay 31 and fitting insert 37 are positively pressed onto one another. Because of the certain resilience of the plastics material of the inlay 31, sealing ring 35 and fitting insert 37, it is to be expected that with complete screwing, these plastics material parts are locally pressed and compressed (in particular by a pressing distance 53), until opposing metal faces meet, so in the completely screwed state, the plastics material and metal faces meet one another in a sealing manner.

Furthermore, FIG. 8 shows the inserted filter 27, which is seated in a recess (the fitting insert 37 here), which recess, toward the through-opening 41, forms a tapering funnel 55. Advantageously, the funnel region 55 remains free of filter material, so a through-flowing medium, when entering the filter region 27, easily distributes through the entire filter diameter and passes at as homogenous a speed as possible via the entire radial region out of the filter 27 into the pipe 11 and/or, coming from the pipe 11, when leaving the filter region 27, can flow away through the through-opening 41 without the formation of a jam in regions.

A configuration of the connection element 13 will be shown in detail below with the aid of FIG. 9. The metal casing 26 comprises the fitting insert 37, which can be inserted from the first end 23. The fitting insert 37 abuts on a first internal shoulder 56 of the metal casing 26. In the cavity of the first end 23, both the fitting insert 37 and the tubular metal casing 26, which has a second internal shoulder 57, form a joint face for a pipe 11 with a sealing ring 35. The two joint faces, according to the view may be configured as joint faces that are approximately flush with one another.

A possible embodiment of the second connection point 24 for the connection of the feed or discharge line is shown in FIG. 9, in particular. The cylindrical recess 58 in the fitting insert 37, which recess 58 serves to receive a feed or discharge line, leads from the through-opening 41 to the opening of the second connection point 25. The inner covering of the feed or discharge line and fitting insert 37 should be able to undergo a positive press connection of plastics material on plastics material here. Following the recess 58, the connection element 13, on the inside, provides at least one portion 59 with a metallic surface to positively receive a metallic casing of a feed or discharge line. The portion 59 may be funnel-shaped in order to ensure a positive and optionally liquid-tight and/or gas-tight connection. This connection can be configured as a screw connection.

A detail of an assembled capillary device, in particular a chromatography column, will be shown below in FIG. 10. The detail given of the device comprises the pipe 11 (i.e. a first capillary), a feed or discharge line 60 (i.e. a second capillary) and a connection element 13. With the aid of the connection element 13, a pipe end region 17 is closed together in a liquid-tight or gas-tight manner with the feed or discharge line 60. A feed or discharge line 60 is constructed of an (advantageously metallic) casing 61 and of an inner covering 62 (such as made of plastics material). The end piece of the feed or discharge line 60 may advantageously carry a connection part 63 for screwing in. A useful connection part 63 may, for example, grip a feed or discharge line 60 if this feed or discharge line 60 is equipped with a thickened end portion 64.

This end portion 64 is thickened and supported, for example, by a ring or a sleeve 65. The ring or sleeve 65 may consist of plastics material. The metal casing 61 in the end portion 64 is expediently slightly shortened compared with the inner covering 62 (advantageously by at least 1 to a maximum of 3 mm), so the inner covering 62 projects in the axial direction. This separate part region of the inner covering 62, also called a sealing portion 66 here, may advantageously undergo a material-uniting connection with the ring or sleeve 65. The material-uniting connection may be achieved in that, for example, the ring or the sleeve 65, which is turned over the end portion 64 during production is glued to the exposed inner covering 62, i.e. the sealing portion 66, and/or welded, for example laser welded, at least where the sealing portion 66 of the feed or discharge line 60 meets the ring or sleeve 65. Alternatively, the ring or the sleeve 65 can be produced in that the end portion 64, in particular with the sealing portion 66, has a plastics material layer injected round it, so a material-uniting connection can optionally be produced at least between the plastics material inner covering 62 of the sealing portion 66 and the injected-on plastics material of the ring or the sleeve 65. In order to promote the integral connection, a laser welding step may additionally be carried out with or after the injection-molding there around.

The connection part 63 is fitted with a widened cone 67, which is, on the one hand, suitable to prevent the feed or discharge line 60 thickened at the end (i.e. end portion 64) from being pulled out and allows a precisely fitting seat in the connection element 13. The cone 67 may be configured with a pipe extension 69, which encompasses the running-in line end over a certain region and supports it. In particular, the cone 67 may be made of metal in order to produce a metal-metal seal with the connection element 13. The transition from the fitting insert 37 to the feed or discharge line 60 is therefore also inwardly tightly closed (in a liquid-tight, optionally gas-tight manner) by a plastics material-plastics material connection and closed outwardly by a metal-metal connection.

To summarise, the assembled capillary device (in particular according to FIG. 10) contains a pipe 11, a feed or discharge line 60 and a connection element 13. The device is distinguished, in particular, in that it has tight (liquid-tight, optionally gas-tight) connection points, at which plastics material is pressed together on plastics material in a sealing manner. These points are firstly the contact face A between the sealing ring 35 and fitting insert 37 and, secondly, the contact face B between the ring or sleeve 64 of the feed or discharge line 60 and the fitting insert 37. The device is furthermore distinguished in that it has tight connection points, at which metal is pressed together on metal in a sealing manner. These points are firstly the contact face C between the support web 51 and the base body 26 of the connection element 13 (or optionally another face between the pipe casing 29 and connection element 13) and, secondly, the contact face D between the cone 67 and base body 26 of the connection element 13. At least the portions of these contact faces mentioned, which do not run parallel to the axial direction, have a sealing effect because of pressing forces.

Exemplary Embodiment

In one exemplary embodiment, a bio-inert HPLC column according to the invention consists of a metal column, in particular a high-grade steel column, with a fitted-in PAEK pipe inlay (in particular a PEEK pipe inlay). The inside is chemically sealed, i.e. in a liquid-tight and optionally gas-tight manner, (for example PEEK/PEEK) and the outside is sealed in a pressure-tight manner or hydraulically (metal/metal).

In order to chemically seal a gap between the PEEK inlay and high-grade steel column, a PEEK ring is fastened on the column end part on both sides as a seal with the aid of laser welding on the inlay.

The fittings consist of high-grade steel on the outside and of a pressed-in PEEK insert on the inside. Thus the sealing takes place with the PEEK column seal on the inside and with the metal edge of the column on the outside. The capillary connection of the fitting is also sealed chemically (PEEK/PEEK) on the inside and is hydraulically tight (metal/metal) on the outside.

The system according to the invention, on the inside, in other words in the region which comes into contact with the sample, may consist completely of a PAEK material (for example, of PEEK). The sample thus only comes into contact with PAEK, in particular PEEK, and a chemical HPLC sample seal is furthermore achieved (in particular only by PEEK).

Thus the system according to the invention has all the advantages which a pure HPLC-PEEK system described at the outset entails.

The external diameter may consist completely of high-grade steel. A hydraulically pressure-tight high-grade steel housing is thus produced, which provides all the advantages of a pure high-grade steel column described at the outset.

To summarise, the system according to the invention has the following advantageous properties:

On the outside, a closed high-grade steel casing exists. Different parts are screwed in a pressure-tight manner, for example by means of fittings.

On the inside, i.e. on the sample side, all the faces are 100% metal-free.

On the inside, only the high temperature-resistant plastics material used, in particular only one type of high temperature-resistant plastics material, comes into contact with the sample material. The insides may only consist of PEEK.

The system is highly bio-inert.

No ion exchange can occur between the sample and the high-grade steel casing.

The torque power of the fittings corresponds to that of a thread torque of high-grade steel.

The stability of the system is guaranteed up to a pressure of 1000 bar and higher.

Because of the high-grade steel casing placed on the outside, the system is pressure tight or hydraulically tight on the outside and because of the plastics material that is welded, glued, pressed and/or applied by being injection-molded around, the system is chemically tight or materially-united on the inside, so that no liquid and optionally no gas can penetrate.

The production process of the bio-inert HPLC column according to the invention expediently contains the following steps:

A metal casing, in particular configured as a high-grade steel pipe, containing two end faces and an inner face with at least a first internal diameter and a certain length, is provided to produce a column.

An inlay made of plastics material (for example a PAEK pipe, such as a PEEK pipe) is inserted or fitted into the internal diameter of the metal casing. An inlay is used here, which is longer than the metal casing, or which is at least longer than the inner face with the first internal diameter of the metal casing in its longitudinal extent.

A sealing ring is placed in or pressed onto the end faces of the metal casing and adjacent to the inlay. The sealing ring also consists of plastics material (for example of a PAEK, or PEEK).

The sealing ring is then advantageously welded to the inlay, for example by laser welding (alternatively, a ring of plastics material can be injected (i.e. by injection-molding)), so that the inlay and sealing ring combined, at the end face on the two column ends, in each case form a sealing face, which is used as a transition to a fitting. These sealing faces are advantageously located in front of the respective end faces of the metal casing.

In a particularly advantageous production process of the bio-inert HPLC column according to the invention, the production process expediently contains the following steps:

A metal casing, in particular configured as a high-grade steel pipe, is advantageously provided with an inner depression on both sides on the pipe ends or casing ends.

An inlay made of plastics material (for example a PAEK pipe, or a PEEK pipe) is inserted or fitted into the internal diameter of the column.

A sealing ring is placed in or pressed into the depression of the metal casing and adjacent to the inlay. The sealing ring also consists of plastics material (for example of a PAEK, or PEEK).

The sealing ring is then advantageously welded to the inlay, for example by laser welding (alternatively, a ring of plastics material can be injected (i.e. by injection-molding)), so that the inlay and sealing ring combined, at the end face on the two column ends, in each case form a sealing face, which is used as a transition to a fitting.

The production process of a bio-inert HPLC screw connection (also called an HPLC fitting here) can proceed as follows:

A cylindrical pipe-shaped metal body, in particular a high-grade steel body, is machined by turning and provided at each end with an internal thread.

A plastics material inlay, such as a PEEK inlay, is produced, by machining by turning.

A frit, in particular a PEEK frit, is pressed into the inlay.

The inlay, before or after the pressing with the frit, is pressed into the metal body.

In summary, a pipe containing a metal casing 29 with an inlay 31 is disclosed here, which is characterised in that the inlay 31 is configured as a plastics material tube and is pushed or drawn into the metal casing 29 and a sealing ring 35 consisting of plastics material is connected, in each case, to the inlay 31 at the end. Because of said structure, a connection to further system parts is possible, which is carry-over-free, inert on the inside, liquid-tight, optionally gas-tight, and pressure-tight. A connection element and a type of connection to connect the pipe to feed and/or discharge lines of a capillary system are also disclosed. Pipes, connection elements and connections of this type are advantageously used in low and high pressure systems, such as, for example, in an HPLC column. The use of such systems is particularly advantageous in in-vitro diagnostics and in liquid handling applications.

The invention claimed is:

1. A pipe for a chromatography column, comprising:
   a tubular metal casing having a first end and a second end and defining an interior pipe passage, the tubular metal casing defining a first inner annular recess at the first end of the tubular metal casing;
   an inlay comprising a plastic material tube having a first end and second end, the inlay lining the interior pipe passage of the tubular metal casing and extending from proximate the first end of the tubular metal casing to proximate the second end of the tubular metal casing, the first end of the inlay extending through the first inner annular recess to form a first annular channel at the first end of the tubular metal casing; and
   a first plastic material sealing ring positioned around the inlay proximate the first end of the inlay and positioned at least partially within the first annular channel.

2. The pipe of claim 1, wherein the inlay extends through the first sealing ring and is connected thereto in a sealing manner.

3. The pipe of claim 1, wherein the pipe comprises a high performance liquid chromatography column.

4. The pipe of claim 1, further comprising a second inner annular recess at the second end of the tubular metal casing, the second end of the inlay extending through the second inner annular recess to form a second annular channel at the second end of the tubular metal casing, and a second plastic material sealing ring connected to the second end of the inlay and positioned at least partially within the first annular channel.

5. The pipe of claim 1, wherein the pipe is configured for use in at least one of an in-vitro diagnostic system, a chemical analysis system or a preparative instrument.

6. The pipe of claim 1, wherein the first end of the inlay extends from the first end of the metal casing and the first sealing ring adjoins the inlay on an outside of the inlay.

7. The pipe of claim 1, wherein the first sealing ring is applied to at least one of the metal casing or the inlay by injection-molding.

8. The pipe of claim 1, wherein the inlay and first sealing ring are welded together to produce an integral material bond between the inlay and the first sealing ring.

9. The pipe of claim 1, wherein the inlay and the sealing ring are comprised of a thermoplastic material.

10. The pipe of claim 9, wherein the inlay and the sealing ring are comprised of a material selected from the group consisting of fluoroplastics, polyaryletherketones, polyetherketone, polyetheretherketone, polyetherketoneketone, polytetrafluoroethylene, polyetheretherketone or mixtures thereof.

11. The pipe of claim 1, wherein inlay and the first sealing ring are formed from the same plastic material.

12. The pipe of claim 1, wherein a wall thickness of the inlay is in a range from 0.05 mm to 2 mm.

13. The pipe of claim 1, wherein the metal casing is comprised substantially of high-grade steel.

14. The pipe of claim 1, wherein an internal diameter of the metal casing is in the range from 0.5 mm to 10 mm.

15. The pipe of claim 1, wherein an internal diameter of the first sealing ring substantially corresponds to an external diameter of the inlay proximate the first end thereof.

16. The pipe of claim 1, wherein the inlay is attached by at least one of a weld or glue to an inner wall of the first sealing ring.

17. The pipe of claim 1, further comprising a thread formed on an outside of the tubular metal casing on an end portion thereof at the first end.

18. The pipe of claim 1, further comprising a connection element coupled to the first end of the tubular metal casing with a feed or discharge line, the connection element configured to engage with the tubular metal casing to hold the connection element relative to the first sealing ring within an internal surface of the connection element abutting against the first sealing ring to form a seal between the pipe and the connection element.

19. A connection element for connecting a chromatography column with a feed or discharge line, comprising:
   a first tubular metal casing having a first end and a second end, the first end defining a first cavity having first and second internal shoulders and an internal threaded portion formed in the cavity at least partially extending between the first end and the second internal shoulder, the second end defining a second cavity configured as a connector for connecting to a feed or discharge line, the first and second cavities being in fluid communication with one another; and
   a plastic insert having a first end and a second end and a through-opening extending therein between, the second end configured to receive one end of the feed or discharge line, the plastic insert positionable within the first cavity with the second end of the insert abuttable against the first internal shoulder of the first metal casing and the first end of the insert and the second internal shoulder of the tubular metal casing forming an abutting face, the abutting face configured to abut against an end of a pipe for a chromatography column inserted within the first cavity.

20. The connection element of claim 19, wherein the plastic insert defines a filter cavity in the first end of the plastic insert and further comprising a filter inserted in the filter cavity.

21. The connection element of claim 19, wherein the pipe comprises a second tubular metal casing configured for receiving an inlay comprising a plastic material tube having a first end and second end insertable into the second tubular metal casing, and wherein a first plastic material sealing ring is connected to the inlay at the first end of the inlay.

22. The connection element of claim 19, further comprising a filter inserted in the first end of the plastic insert.

23. A chromatography column configured for connecting between a feed line and a discharge line, comprising:
a first tubular metal casing having a first end and a second end;
an inlay comprising a plastic material tube having a first end and second end configured to be insertable into the first metal casing;
a first plastic material sealing ring connected to the inlay proximate the first end of the inlay;
a second plastic material sealing ring connected to the inlay proximate the second end of the inlay;
a first connection element configured for connecting the first end of the first tubular metal casing to a feed line comprising:
a second tubular metal casing having a first end, a second end, a cavity at the first end defining first and second internal shoulders and an internal thread formed in the cavity, the second end being configured as a connector for the feed line;
a first center piece comprising a first plastic material pressed body with a through-opening to receive one end of the feed line, the first plastic material pressed body insertable into the cavity from the first end and abuttable against the first internal shoulder of the second metal casing, the plastic material pressed body and the second internal shoulder of the second tubular metal casing forming a first abutting face;
a second connection element configured for connecting the second end of the first tubular metal casing to a discharge line comprising:
a third tubular metal casing having a first end, a second end, a cavity at the first end defining first and second internal shoulders and an internal thread formed in the cavity, the second end being configured as a connector for the discharge line;
a second center piece comprising a second plastic material pressed body with a through-opening to receive one end of the discharge line, the first plastic material pressed body insertable into the cavity from the first end and abuttable against the first internal shoulder of the third metal casing, the second plastic material pressed body and the second internal shoulder of the third tubular metal casing forming an second abutting face.

24. The chromatography column of claim 23, further comprising a first filter inserted in the first end of the plastic material pressed body of the first connection element.

25. The chromatography column of claim 24, wherein the first filter is positioned between the inlay and the first plastics material pressed body.

26. The chromatography column of claim 25, wherein the first filter is comprised of at least one of a filter fabric, a screen or a frits.

27. The chromatography column of claim 25, wherein an external diameter of the first plastics material pressed body substantially corresponds to the external diameter of the first sealing ring.

28. The chromatography column of claim 25, wherein a first seal of plastic on plastic is formed between the first and second connection elements and the inlay and a second seal of metal on metal is formed between each of the first and second connection elements and the first tubular metal casing.

29. The chromatography column of claim 28, wherein the first and second plastic on plastic seals each form an inner seal and the first and second metal on metal seals each form an outer seal.

30. The chromatography column of claim 25, wherein the feed line and discharge line each comprise a plastic material tube having a metal surround.

31. The chromatography column of claim 25, wherein a first plastic on plastic seal and a first metal on metal seal is formed between the first connection element and the feed line and a second plastic on plastic seal and a second metal on metal seal is formed between the second connection element and the discharge line.

32. The chromatography column of claim 25, wherein the chromatography column comprises a high performance liquid chromatography column.

33. The chromatography column of claim 25, wherein the chromatography column is a component of an in-vitro diagnostic system or a liquid handling system.

34. The chromatography column of claim 25, wherein the chromatography column is a component of at least one of a low or high pressure line system.

35. A connection element for connecting a chromatography column with a feed or discharge line, comprising:
a first tubular metal casing having a first end, a second end, a cavity at the first end defining first and second internal shoulders and an internal thread formed in the cavity, the second end being configured as a connector for a feed or discharge line, wherein the first end of the first tubular metal casing is configured to attach to a first end of a second tubular metal casing and wherein the second tubular metal casing is configured for receiving an inlay comprising a plastic material tube having a first end and second end insertable into the second tubular metal casing, and wherein a first plastic material sealing ring is connected to the inlay at the first end of the inlay; and
a first center piece comprising a first plastic material pressed body with a through-opening to receive one end of the feed or discharge line, the first plastic material pressed body insertable into the cavity from the first end and abuttable against the first internal shoulder of the first metal casing, the plastic material pressed body and the second internal shoulder of the tubular metal casing forming an abutting face.

* * * * *